(12) United States Patent
Shibuya et al.

(10) Patent No.: US 10,408,811 B2
(45) Date of Patent: Sep. 10, 2019

(54) CRUDE OIL COMPOSITION ESTIMATION METHOD, ABSORPTION PROCESS SIMULATION METHOD IN ABSORPTION AND LIQUEFACTION SYSTEM, PROCESS SIMULATION METHOD IN RECOVERY SYSTEM, AND METHOD OF PRODUCING ABSORPTION AND LIQUEFACTION SYSTEM

(71) Applicant: JFE Engineering Corporation, Tokyo (JP)

(72) Inventors: Yoshiki Shibuya, Tokyo (JP); Kengo Murai, Tokyo (JP)

(73) Assignee: JFE Engineering Corporation, Tokyo (JP)

( * ) Notice: Subject to any disclaimer, the term of this patent is extended or adjusted under 35 U.S.C. 154(b) by 1015 days.

(21) Appl. No.: 14/871,823

(22) Filed: Sep. 30, 2015

(65) Prior Publication Data
US 2016/0252489 A1    Sep. 1, 2016

(30) Foreign Application Priority Data
Feb. 27, 2015    (JP) .................. 2015-038569

(51) Int. Cl.
*G01N 33/28*    (2006.01)
*G16C 20/30*    (2019.01)

(52) U.S. Cl.
CPC ......... *G01N 33/2841* (2013.01); *G16C 20/30* (2019.02)

(58) Field of Classification Search
CPC .................................................. G01N 33/2841
See application file for complete search history.

(56) References Cited

U.S. PATENT DOCUMENTS 1,621,821 A    3/1927  Armstrong
4,066,423 A    1/1978  McGill et al.
(Continued)

OTHER PUBLICATIONS

Ajayi, Adebayo, Habiba Shehu, and Edward Gobina. "Recovery of VOC from onshore and offshore shuttle tankers using structured membranes." (2015). 6 pages (Year: 2015).*

(Continued)

*Primary Examiner* — Omar F Fernandez Rivas
*Assistant Examiner* — Robert S Brock
(74) *Attorney, Agent, or Firm* — McDermott Will & Emery LLP

(57) ABSTRACT

A crude oil composition estimation method estimates a composition of crude oil for use in simulation of a material balance in an absorption and liquefaction system that absorbs vapors emitted from the crude oil with the crude oil. The crude oil composition estimation method includes: comparing a calculated concentration of a treated gas with a measured concentration of the treated gas; estimating, when the calculated concentration agrees with the measured concentration, that the concentration included in the crude oil is a correct crude oil composition; and repeating, when the calculated concentration does not agree with the measured concentration, a process of correcting the concentration included in the crude oil and then comparing the calculated concentration with the measured concentration, until the calculated concentration agrees with the measured concentration, and when they agree, estimating that the corrected concentration in the crude oil is a correct crude oil composition.

10 Claims, 4 Drawing Sheets

(56) References Cited

U.S. PATENT DOCUMENTS

| | | | |
|---|---|---|---|
| 4,549,958 A | | 10/1985 | Beck et al. |
| 4,772,295 A | | 9/1988 | Kato et al. |
| 5,163,982 A | * | 11/1992 | de Andrade Bruuning ................ G01N 33/2829 210/635 |
| 5,350,503 A | | 9/1994 | Freymeyer et al. |
| 5,678,423 A | * | 10/1997 | Davies ............... B01D 53/1487 62/613 |
| 6,087,662 A | | 7/2000 | Wilt et al. |
| 6,165,253 A | * | 12/2000 | Sirkar .................... B01D 53/14 96/6 |
| 9,934,367 B2 | * | 4/2018 | Chen .................. G01N 33/2823 |
| 2004/0221718 A1 | * | 11/2004 | Grodal ................... B65D 90/30 95/90 |
| 2009/0294331 A1 | * | 12/2009 | Sahara ............... B01D 53/1493 208/299 |
| 2010/0204925 A1 | * | 8/2010 | Albahri .................. G01N 25/14 702/25 |
| 2011/0264415 A1 | * | 10/2011 | Bleackley ........... G06F 17/5004 703/1 |
| 2011/0313739 A1 | * | 12/2011 | Mahalec ................ G05B 17/02 703/2 |
| 2015/0073188 A1 | * | 3/2015 | Floudas ............... C10G 29/205 585/332 |

OTHER PUBLICATIONS

Choi, M. S. "API tank vapors project." In SPE Annual Technical Conference and Exhibition. Society of Petroleum Engineers, 1993. pp. 791-798 (Year: 1993).*

Krishnamurthy, R., and R. Taylor. "Absorber simulation and design using a nonequilibrium stage model." The Canadian Journal of Chemical Engineering 64, No. 1 (1986): 96-10 (Year: 1986).*

Lee, Sangick, Inhwan Choi, and Daejun Chang. "Multi-objective optimization of VOC recovery and reuse in crude oil loading." Applied energy 108 (2013): 439-447. (Year: 2013).*

Martens, Otto M., Ole Oldervik, Bengt Olav Neeraas, and Terje Strøm. "Control of VOC emissions from crude oil tankers." Paper presented at the 8th ICMES/SNAME New York Metropolitan Section Symposium in New York, May 22-23, 2000. 12 pages (Year: 2000).*

Martens, Otto M., Ole Oldervik, Bengt Olav Neeraas, and Terje Strøm. "Control of VOC emissions from crude oil tankers." Marine Technology 38, No. 3 (2001): 208-217. (Year: 2001).*

Oyelakin et al. "Mathematical Modeling and Experimental Breakthrough Curves for the Adsorption of Toxic Vapors Emitted from Crude Oil and Condensate Storage Tanks." In SPE Annual Technical Conference and Exhibition. Society of Petroleum Engineers, 2015. 27 pages (Year: 2015).*

Shibuya Yoshiki, Vapor Recovery Technique for Crude Oil Ship Loading—Spray Absorption, JFE No. 32 (Mar. 2014) pp. 79-86 (Year: 2014).*

Shibuya Yoshiki, Vapor Recovery Technique for Crude Oil Ship Loading—Spray Absorption, JFE Technical Report No. 19 (2013) pp. 158-166 (Year: 2013).*

Stuckey Jr, A. Nelson, and Wayne C. Edmister. "Vapor-Liquid Equilibria of a Methane-Condensate System Using Chromatographic Assays." In Fall Meeting of the Society of Petroleum Engineers of AIME. Society of Petroleum Engineers, 1965. (Year: 1965).*

Tamaddoni, Maryam, Rahmat Sotudeh-Gharebagh, Shunji Nario, Mehdi Hajihosseinzadeh, and Navid Mostoufi. "Experimental study of the VOC emitted from crude oil tankers." Process Safety and Environmental Protection 92, No. 6 (2014): 929-937. (Year: 2014).*

Notice of Rejection Japanese Patent Application No. 2015-038569 dated Mar. 24, 2015 with English translation.

Decision of a Patent Grant Japanese Patent Application No. 2015-038569 dated Jun. 16, 2015 with English translation.

GCC Office Action issued in corresponding GCC Patent Application No. 2015-30064, dated Feb. 21, 2019.

* cited by examiner

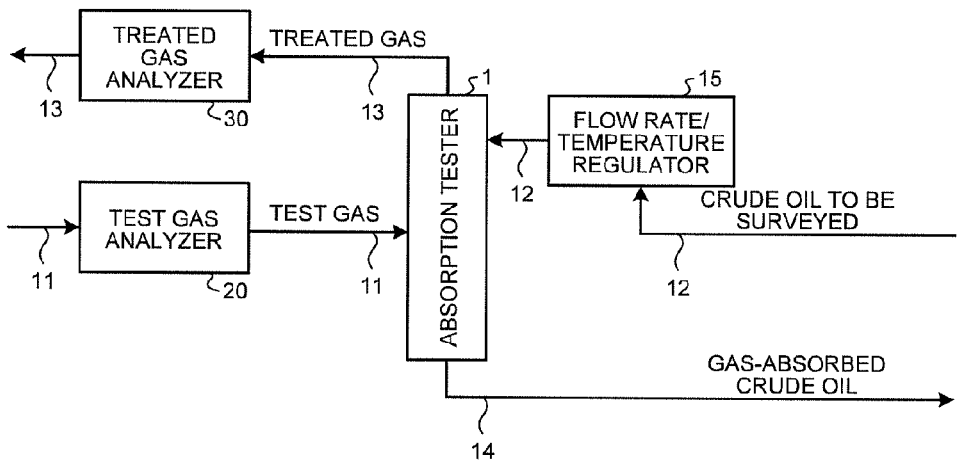

CRUDE OIL COMPOSITION ESTIMATION METHOD, ABSORPTION PROCESS SIMULATION METHOD IN ABSORPTION AND LIQUEFACTION SYSTEM, PROCESS SIMULATION METHOD IN RECOVERY SYSTEM, AND METHOD OF PRODUCING ABSORPTION AND LIQUEFACTION SYSTEM

CROSS-REFERENCE TO RELATED APPLICATIONS

This application is based upon and claims the benefit of priority from Japanese Patent Application No. 2015-038569, filed Feb. 27, 2015, the entire contents of which are incorporated herein by reference.

BACKGROUND OF THE INVENTION

1. Field of the Invention

The present invention relates to a crude oil composition estimation method, an absorption process simulation method in an absorption and liquefaction system, a process simulation method in a recovery system, and a method of producing an absorption and liquefaction system.

2. Description of the Related Art

Conventionally, vapors emitted into the air, for example, in the process of transporting crude oil have been one of large emission sources of volatile organic compounds (VOC). As an approach to environmental problems and energy problems, there is a growing need for absorption and liquefaction systems that recover volatile organic compounds by absorbing and liquefying them with absorption oil. As an example of absorption and liquefaction systems, a technique as illustrated in FIG. 5 is known in which VOC-containing vapors are brought into countercurrent contact with absorption oil and thereby liquefied and recovered (for example, see U.S. Pat. No. 1,621,821). The technique has a room for improvement in efficiency of recovery of volatile organic compounds. As illustrated in FIG. 6, a technique for improving the recovery efficiency is known, in which the pressure swing adsorption (PSA) process using an adsorbent (activated carbon) that selectively adsorbs hydrocarbons is used simultaneously with absorption and liquefaction (for example, see U.S. Pat. No. 4,066,423). As illustrated in FIG. 7, a technique is known which additionally uses a gas separation membrane that allows hydrocarbons to selectively pass through (for example, see U.S. Pat. No. 4,772,295).

Absorption and liquefaction systems using crude oil as absorption oil are also known. To design such an absorption and liquefaction system, the material balance in the absorption and liquefaction system need to be simulated based on the composition of vapors (gas) and the composition of crude oil (liquid). Here, the composition refers to the included components and concentrations thereof. In the simulation, the composition after an absorption and liquefaction process is estimated by performing vapor-liquid equilibrium calculation based on the composition of vapors and the composition of crude oil. In order to obtain a precise simulation result, the accurate compositions of vapors and crude oil are required.

The analysis of compositions of crude oil, however, requires enormous time and effort because a number of components are included in crude oil. Moreover, the analysis result obtained with time and effort does not necessarily have high reproducibility.

The properties of crude oil are found in, for example, open data such as the HMC-4A database released by Hydrocarbon Management Committee (HMC) and the American Petroleum Institute (API) organized according to oil kinds and producing areas, released by oil-related companies. Some process simulators for simulating an absorption process have the function of creating a simulated composition (crude oil simulated composition creating function) using a component represented by the boiling point based on a distillation curve as a hypothetical component of crude oil. Thus, even when the composition is unknown, a series of process simulations can be done by creating a simulated composition with hypothetical components with a process simulator based on open data, and using the created simulated composition. The simulated composition, however, differs from the composition of actual chemical substance components (hydrocarbon components) and therefore has a room for improvement in precision when used in simulation. The reason for this is that vapor-liquid equilibrium calculation cannot be accurately performed because the composition of vapors includes actual chemical substance components whereas the composition of crude oil includes hypothetical components.

The inventors of the subject application have conducted detailed analysis and examination on vapor compositions of crude oil. The inventors have found that vapors of crude oil include similar components irrespective of producing areas and other factors. The inventors have examined light components that have a large effect on the absorption operation among the components included in crude oil. The inventors have found that any crude oil has almost the same light components. Based on the result of such analysis and examination, the inventors of the subject application have found that accurately knowing the concentration for each typical component (composition of crude oil) in a crude oil composition table leads to a simulation with high precision.

In the absorption operation, a large amount of crude oil is usually used for allowing plenty of absorption capability in order to recover a maximum amount of hydrocarbon components in vapors. Thus, the difference between the compositions of crude oil before and after absorption is found to be extremely small when analyzed in the liquid phase. It is therefore difficult to estimate the composition of crude oil from the result of analysis in the liquid phase. By contrast, in the vapor phase, the analysis of light components is easy and, in addition, there are significant changes in composition before and after absorption because most of hydrocarbon components are absorbed. As a result, the amount of each component absorbed can be grasped precisely. Based on these, the inventors of the subject application have found that the composition of crude oil can be estimated from the analyzed values of light components in the vapor phase in the process of hydrocarbon absorption from vapors with crude oil.

There is a need for a crude oil composition estimation method of estimating the composition of crude oil for achieving a precise simulation result, an absorption process simulation method in an absorption and liquefaction system, a process simulation method in a recovery system, and a method of producing an absorption and liquefaction system.

SUMMARY OF THE INVENTION

A crude oil composition estimation method of estimating a composition of crude oil for use in simulation of a material balance in an absorption and liquefaction system that absorbs vapors emitted from the crude oil with the crude oil may include: performing an absorption test of absorbing test gas of the vapors with the crude oil and measuring concentration for each component of the test gas and concentration for each component of treated gas discharged after part of the test gas is absorbed with the crude oil; creating a simulated composition of the crude oil with a composition of a concentration for each hypothetical component represented by a boiling point, based on crude oil open data indicating properties of the crude oil; setting a concentration for each component included in the crude oil obtained by substituting hypothetical components of the created simulated composition of the crude oil with respective corresponding actual hydrocarbon components, as input values to a simulation; simulating a material balance of an absorption process of absorbing the test gas with the crude oil in the absorption test, based on the concentration for each component included in the crude oil and the concentration for each component of the test gas measured in the absorption test; comparing the concentration for each component of the treated gas calculated by the simulation with the concentration for each component of the treated gas measured in the absorption test; estimating, at a time the concentration for each component of the treated gas calculated by the simulation agrees with the concentration for each component of the treated gas measured in the absorption test, that the concentration for each component included in the crude oil is a correct crude oil composition; and repeating, at a time the concentration for each component of the treated gas calculated by the simulation does not agree with the concentration for each component of the treated gas measured in the absorption test, a process of correcting the concentration for each component included in the crude oil and then comparing the concentration for each component of the treated gas calculated by the simulation with the concentration for each component of the treated gas measured in the absorption test, until the concentration for each component of the treated gas calculated by the simulation agrees with the concentration for each component of the treated gas measured in the absorption test, and, at a time there is an agreement, estimating that the corrected concentration for each component included in the crude oil is a correct crude oil composition.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 1 is a block diagram illustrating an overview of an absorption process according to an embodiment;

FIG. 2 is a schematic diagram illustrating a composition table in which components of crude oil are represented by hypothetical components;

DETAILED DESCRIPTION OF THE PREFERRED EMBODIMENTS

Figure 3:
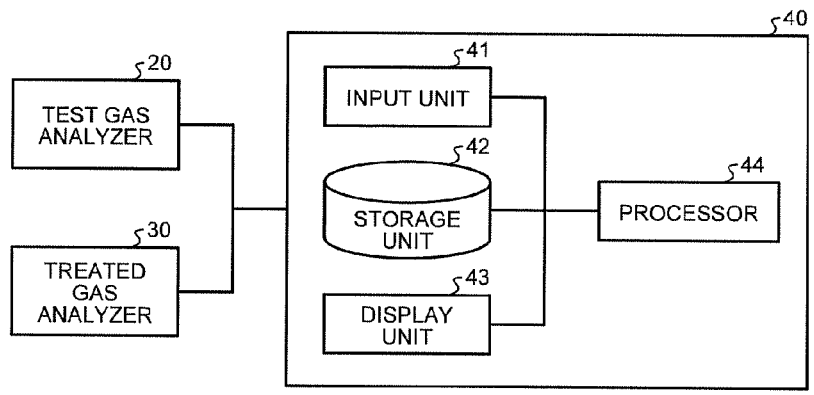
FIG. 3 is a schematic block diagram illustrating a process simulator.

An embodiment of a crude oil composition estimation method, an absorption process simulation method in an absorption and liquefaction system, and a process simulation method in a recovery system according to the present invention will be described below in detail in conjunction with the figures. It should be noted that the present embodiment is not intended to limit this invention.

Referring to FIG. 1 to FIG. 4, an embodiment will be described. The present embodiment relates to a crude oil composition estimation method, an absorption process simulation method in an absorption and liquefaction system, and a process simulation method in a recovery system. The crude oil composition estimation method is a method of estimating the concentration for each component of crude oil from the concentration for each component (composition) in the vapor phase when part of test gas of vapors (test sample gas) is absorbed with crude oil to be surveyed as absorption oil (hereinafter simply referred to as crude oil) in an absorption tester 1.

The absorption tester 1 performs, for example, an absorption test for reproducing an absorption process equivalent to an absorption process in an absorption and liquefaction system in which vapors of crude oil discharged from the hold of a tanker are absorbed and liquefied with crude oil and thereby recovered. The absorption tester 1 has the functions and configuration equivalent to those of an absorption and liquefaction system. The absorption tester 1 is a simple device produced by simplifying and reducing the size of an absorption and liquefaction system. As illustrated in FIG. 1, the absorption tester 1 performs an absorption test in which the same vapors (test gas) of crude oil as those absorbed and liquefied in an absorption and liquefaction system are absorbed with crude oil. The absorption tester 1 is a cylindrical absorption column (packed column) having an inner diameter of several tens of millimeters and an axial length of several tens to several hundreds of millimeters. The absorption tester 1 produces a steady state through concurrent contact continuous absorption in multistage vapor-liquid equilibrium in the inside thereof. With the multistage vapor-liquid equilibrium state, the absorption tester 1 can simulate (absorption process simulation) the material balance of the absorption process with a process simulator 40 described later. Specifically, for example, the concentration for each component (composition) of the treated gas is calculated by simulating the material balance of the absorption process in the absorption tester 1 through multistage vapor-liquid equilibrium calculation based on, for example, the Benedict-Webb-Rubin (BWR) equation.

The absorption tester 1 is mainly connected with a first pipe 11, a second pipe 12, a third pipe 13, and a fourth pipe 14. The first pipe 11 supplies test gas to the absorption tester 1. The second pipe 12 supplies crude oil to the absorption tester 1. The second pipe 12 is connected with a pump for introducing crude oil to the top of the absorption tester 1. The third pipe 13 discharges the treated gas from the absorption tester 1 after part of the test gas is absorbed with crude oil. The fourth pipe 14 discharges the gas-absorbed crude oil that has absorbed part of the test gas, from the absorption tester 1. A flow rate/temperature regulator 15 is disposed on the channel of the second pipe 12. The flow rate/temperature regulator 15 regulates the flow rate and the temperature of crude oil. The flow rate/temperature regulator 15 is configured with, for example, a valve and a thermostat. In the present embodiment, the flow rate of test gas is set to 20 to 200 NL/min. The flow rate of crude oil is set to 0.3 to 3 L/min. The temperature of the inside of the absorption tester 1 (the temperature in the absorption operation (temperature condition)) is set to room temperature to 60° C. The amount of absorption decreases as the temperature inside the absorption tester 1 increases. The pressure in the absorption operation (pressure condition) is set to atmospheric pressure to 0.5 MPa. The absorption tester 1 as described above is installed in a place where an absorption and liquefaction system is scheduled to be installed. If this is not feasible, an absorption test may be conducted in an appropriate test room in which crude oil is brought, although the precision may be lowered to some extent.

A test gas analyzer 20 analyzes the components of test gas and is disposed at the inlet of test gas from the first pipe 11 to the absorption tester 1. The test gas analyzer 20 is configured with, for example, a gas chromatograph for analyzing hydrocarbon components, a galvanic cell-type oxygen analyzer for analyzing oxygen components, and an Orzat analyzer and an infrared analyzer for analyzing other components. The test gas analyzer 20 transmits test gas analysis data including the concentration for each component of the analyzed test gas to the process simulator 40 described later. A treated gas analyzer 30 analyzes the components of the treated gas and is configured similarly to the test gas analyzer 20. The treated gas analyzer 30 is disposed at the outlet of the treated gas from the absorption tester 1 to the third pipe 13. The treated gas analyzer 30 transmits treated gas analysis data including the concentration for each component of the analyzed treated gas to the process simulator 40 described later.

The process simulator 40 has the function of simulating an absorption process in the absorption tester by the absorption process simulation method and estimates the composition of crude oil based on the simulation result. As illustrated in FIG. 3, the process simulator 40 is a processing apparatus including a computer mainly including an input unit 41, a storage unit 42, a display unit 43, and a processor 44. The process simulator 40 receives the test gas analysis data from the test gas analyzer 20 and receives the treated gas analysis data from the treated gas analyzer 30.

The input unit 41 inputs to the process simulator 40, for example, the analysis data of test gas, the treated gas analysis data, crude oil open data, the flow rate of test gas, the flow rate of crude oil, and the temperature and the pressure during an absorption test in the absorption tester 1. The input unit 41 is connected to the test gas analyzer 20 and the treated gas analyzer 30. The input unit 41 is configured with an input device such as a keyboard and a mouse.

The storage unit 42 is configured with a storage device such as a volatile memory, a nonvolatile memory, and a magnetic disk. The storage unit 42 stores the test gas analysis data, the treated gas analysis data and crude oil open data input through the input unit 41, simulation results, and a program and tasks necessary for information processing in the process simulation in the process simulator 40.

The display unit 43 is configured with a display device such as a display and an output device such as a printer. The display unit 43 displays or outputs the simulation result in the process simulator 40.

The processor 44 mainly has the crude oil simulated composition creating function of creating a simulated composition of crude oil based on crude oil open data, the function (simulation function) of simulating the material balance of the absorption process in the absorption tester by the absorption process simulation method, and the function (crude oil composition estimating function) of estimating the composition of crude oil by the crude oil composition estimation method. Here, in the absence of the crude oil composition estimating function, the composition of crude oil may be estimated by correcting an input value by trial and error. The details will be described later.

Test gas of the same vapors as those absorbed and liquefied in the absorption and liquefaction system is pressurized and used as the test gas. If test gas is not available, a cylinder of standard gas including typical components in a crude oil composition table is prepared and used for an absorption test.

The concentration for each component of crude oil is estimated based on the difference between the concentration for each component of the test gas and the concentration for each component of the treated gas.

TABLE 1

| Carbon number | Component | Test sample gas vol % | 24° C. Treated gas vol % |
|---|---|---|---|
| C1 | Methane | 0.62 | 0.52 |
| C2 | Ethane | 1.36 | 0.97 |
| C3 | Propane | 6.12 | 2.71 |
| C4 | iso-Butane | 1.65 | 0.55 |
|  | n-Butane | 4.71 | 1.51 |
| C5 | iso-Pentane | 1.57 | 0.39 |
|  | n-Pentane | 1.80 | 0.47 |
| C6 | 2-Methylpentane | 0.03 | 0.00 |
|  | n-Hexane | 0.74 | 0.15 |
|  | Cyclohexane | 0.40 | 0.07 |
|  | Benzene | 0.77 | 0.17 |
| C7 | 2-Methylhexane | 0.10 | 0.01 |
|  | n-Heptane | 0.05 | 0.00 |
|  | Methylcyclohexane | 0.02 | 0.00 |
|  | Toluene | 0.06 | 0.00 |
| C8 | 2-Methylheptane | 0.00 | 0.00 |
|  | n-Octane | 0.00 | 0.00 |
|  | Ethylcyclohexane | 0.00 | 0.00 |
|  | p-Xylene | 0.00 | 0.00 |
| C9 | 2-Methyloctane | 0.00 | 0.00 |
|  | n-Nonane | 0.00 | 0.00 |
|  | 1,2,4-Trimethylcyclohexane | 0.00 | 0.00 |
|  | 1,2,4-Trimethylbenzene | 0.00 | 0.00 |
| C10 | 2-Methylnonane | 0.00 | 0.00 |
|  | n-Decane | 0.00 | 0.00 |
|  | 1,2-Diethylcyclohexane | 0.00 | 0.00 |
|  | Naphthalene | 0.00 | 0.00 |
| — | Total hydrocarbons | 20.02 | 7.53 |

Table 1 lists the concentrations in the test gas obtained by analysis during an absorption test under a temperature condition of 24° C. and the concentrations in the treated gas obtained by analysis. In this example, the concentration for each component of the test gas is all reduced in the treated gas. Specifically, the concentration of the sum of hydrocarbons (total hydrocarbons) of the test gas is 20.02 vol %, and the concentration of the sum of hydrocarbon components of the treated gas is 7.53 vol %. The amount of reduction in concentration for each component of the test gas is thought to be absorbed into the crude oil. That is, the crude oil is thought to have an absorption capacity equivalent to the amount of reduction in concentration for each component of the test gas. As described above, the concentration for each component of the crude oil is estimated based on the difference between the concentration for each component of the test gas and the concentration for each component of the treated gas.

A component having a concentration higher than zero in the test gas and having a concentration of zero in the treated gas is thought to be completely absorbed in the crude oil. In such a case, the concentration for each component of crude oil cannot be estimated accurately. Absorption tests are then performed under different temperature conditions, and respective pairs of the concentration for each component of the test gas and the concentration for each component of the treated gas are acquired. The concentrations of some components of the crude oil are then estimated based on the difference between the concentration for each component of the test gas and the concentration for each component of the treated gas at a first temperature. The concentrations of other components of the crude oil are then estimated based on the difference between the concentration for each component of the test gas and the concentration for each component of the treated gas at a temperature different from the first temperature.

Specifically, as listed in Table 1, in an absorption test under a temperature condition of 24° C., the concentration of $C_6$ 2-methylpentane is 0.03 vol % in the test gas and 0.00 vol % in the treated gas. In the absorption test under a temperature condition of 24° C., 2-methylpentane is thus completely absorbed into crude oil, so that the concentration for each component of the crude oil cannot be estimated accurately. The temperature in the absorption operation is then set to 36° C. so that the amount of absorption is reduced when compared with the absorption test under a temperature condition of 24° C. The concentration of 2-methylpentane in the treated gas is thus increased to greater than zero.

Table 2 lists the concentrations in the test gas obtained by analysis during an absorption test under a temperature condition of 36° C. and the concentrations in the treated gas obtained by analysis. In an absorption test under a temperature condition of 36° C., the concentration of 2-methylpentane is 0.02 vol % in the test gas and 0.01 vol % in the treated gas. As described above, the concentration of 2-methylpentane in the crude oil can be estimated more accurately based on the concentration of 2-methylpentane in the absorption test under a temperature condition of 36° C. Similarly, for $C_7$ n-heptane and toluene and $C_8$ 2-methylheptane and p-xylene, the concentration for each component of the crude oil can be estimated accurately based on the concentration for each component in the absorption test under a temperature condition of 36° C. That is, the absorption capacity of the crude oil is estimated from the amount of change in concentration for each component of the tested gas under a temperature condition of 36° C. As described above, for a component that is completely absorbed into crude oil in an absorption test under a certain temperature condition so that the concentration for each component of crude oil cannot be estimated accurately, the corresponding concentration for each component of crude oil is estimated based on the difference between the concentration for each component of the test gas and the concentration for each component of the treated gas in an absorption test under a different temperature condition. The concentration of methane under a temperature condition of 36° C. is 0.99 vol % in the test gas and 1.03 vol % in the treated gas. This means that almost no methane is absorbed, and an absorption test result under a temperature condition of 24° C. is necessary as to the capacity of absorbing methane.

The same crude oil as the one absorbed and liquefied in the absorption and liquefaction system is used as the crude oil. Crude oil mainly contains hydrocarbon components and additionally includes nitrogen, oxygen, and carbon dioxide as listed in the composition table. Examples of hydrocarbon components of crude oil include $C_1$ methane, $C_2$ ethane, $C_3$ propane, $C_4$ iso-butane and n-butane, $C_5$ iso-pentane, n-pentane, and 2,2-dimethylbutane, $C_6$ 2-methylpentane, n-hexane, cyclohexane, and benzene, $C_7$ 2-methylhexane, n-heptane, methylcyclohexane, and toluene, $C_9$ 2-methylheptane, n-octane, ethylcyclohexane, p-xylene, and 1,2-dimethylcyclohexane, $C_9$ 2-methyloctane, n-nonane, 1,2,4-trimethylcyclohexane, and 1,2,4-trimethylbenzene, and $C_{10}$ 2-methylnonane, n-decane, 1,2-diethylcyclohexane, and naphthalene. The properties related to crude oil are found in crude oil open data released by public institutions including American Society for Testing and Materials (ASTM) and American Petroleum Institute (API). Examples of crude oil open data include concentrations of light components of crude oil, distillation curve, API gravity, Reid vapor pressure (RVP), and Watson factor.

The crude oil composition estimation method using the absorption tester 1, the absorption process simulation method in an absorption and liquefaction system, and the process simulation method in a recovery system, and the effects thereof will now be described. In the present embodiment, it is assumed that in designing an absorption and liquefaction system in which vapors of crude oil discharged from the hold of a tanker are absorbed and liquefied with

TABLE 2

| Carbon number | Component | Test sample gas vol % | 36° C. Treated gas vol % |
|---|---|---|---|
| C1 | Methane | 0.99 | 1.03 |
| C2 | Ethane | 1.44 | 1.39 |
| C3 | Propane | 5.69 | 4.78 |
| C4 | iso-Butane | 1.75 | 1.15 |
|  | n-Butane | 4.80 | 3.12 |
| C5 | iso-Pentane | 1.40 | 0.80 |
|  | n-Pentane | 1.58 | 0.99 |
| C6 | 2-Methylpentane | 0.02 | 0.01 |
|  | n-Hexane | 0.44 | 0.27 |
|  | Cyclohexane | 0.29 | 0.17 |
|  | Benzene | 0.54 | 0.36 |
| C7 | 2-Methylhexane | 0.07 | 0.03 |
|  | n-Heptane | 0.02 | 0.01 |
|  | Methylcyclohexane | 0.02 | 0.00 |
|  | Toluene | 0.03 | 0.02 |
| C8 | 2-Methylheptane | 0.00 | 0.01 |
|  | n-Octane | 0.00 | 0.00 |
|  | Ethylcyclohexane | 0.00 | 0.00 |
|  | p-Xylene | 0.00 | 0.01 |
| C9 | 2-Methyloctane | 0.00 | 0.00 |
|  | n-Nonane | 0.00 | 0.00 |
|  | 1,2,4-Trimethylcyclohexane | 0.00 | 0.00 |
|  | 1,2,4-Trimethylbenzene | 0.00 | 0.00 |
| C10 | 2-Methylnonane | 0.00 | 0.00 |
|  | n-Decane | 0.00 | 0.00 |
|  | 1,2-Diethylcyclohexane | 0.00 | 0.00 |
|  | Naphthalene | 0.00 | 0.00 |
| — | Total hydrocarbons | 19.08 | 14.15 | crude oil, the composition of crude oil is estimated by the crude oil composition estimation method, and the absorption and liquefaction system is simulated by the absorption process simulation method in an absorption and liquefaction system.

First, the absorption tester 1 is installed in a place where an absorption and liquefaction system is scheduled to be installed. With this absorption tester 1, an absorption test is conducted in which the same vapors (test gas) of crude oil as those absorbed and liquefied in the absorption and liquefaction system are absorbed with the same crude oil. In the absorption tester 1, test gas is supplied from the first pipe 11, and crude oil is supplied from the second pipe 12. From the absorption tester 1, the treated gas is discharged through the third pipe 13, and the gas-absorbed crude oil is discharged through the fourth pipe 14. The flow rate and the temperature of crude oil in an absorption test are regulated by the flow rate/temperature regulator 15. The test gas analyzer 20 analyzes the concentration for each component of the test gas, and the treated gas analyzer 30 analyzes the concentration for each component of the treated gas. The test gas analyzer 20 transmits the test gas analysis data to the process simulator 40. The treated gas analyzer 30 transmits the treated gas analysis data to the process simulator 40. In such an absorption tester 1, a multistage vapor-liquid equilibrium state is established.

An absorption process in the absorption tester is simulated by the absorption process simulation method in the process simulator 40 (simulation function), and the crude oil composition is estimated by the crude oil composition estimation method (crude oil composition estimating function). The simulation function refers to step S13 in the process according to the procedure illustrated in FIG. 4 in the process simulator 40. The crude oil composition estimating function refers to the process (step S11 to step S17) according to the procedure illustrated in FIG. 4 in the process simulator 40.

First of all, crude oil open data including distillation curve, API gravity, and Reid vapor pressure is input to the process simulator 40. A simulated composition of crude oil is then created by the crude oil simulated composition creating function based on the input crude oil open data (step S11). The created simulated composition of crude oil is divided into hypothetical components represented by boiling points (boiling point components) as illustrated in FIG. 2.

In the present embodiment, of the hypothetical components in the simulated composition of crude oil, $C_1$-$C_{10}$ hypothetical components are substituted with actual chemical substance components (hydrocarbon components) (step S12). That is, the concentrations of the $C_{1-10}$ hypothetical components are substituted with the concentrations of hydrocarbon components, assuming that they are actually included in hydrocarbon components. Specifically, for example, as listed in Table 3 described later, the hypothetical components of a boiling point 51° C., a boiling point 77° C., a boiling point 101° C., a boiling point 128° C., and a boiling point 155° C. are substituted with the concentrations of hydrocarbon components, assuming that the concentrations of the hypothetical components are zero. Here, if the actually measured value is available for each range of carbon numbers, the concentration of a hydrocarbon component may be input with reference to that value. If the Watson factor is presented, the proportion of a chain saturated hydrocarbon, a cyclic saturated hydrocarbon, and an aromatic hydrocarbon is estimated, and the concentration of a hydrocarbon component may be input with reference to this value. The composition of the crude oil obtained by substituting the hypothetical components in the created simulated composition of the crude oil with the corresponding actual hydrocarbon components is set as an input value to the simulation function.

The composition of the treated gas and the composition of the gas-absorbed crude oil are calculated by the simulation function simulating the material balance of the absorption process in the absorption tester 1 through vapor-liquid equilibrium calculation, based on the composition of the analyzed test gas, the composition of the crude oil obtained and input by substituting the hypothetical components in the simulated composition of crude oil with the corresponding actual hydrocarbon components, the flow rate of the test gas, the flow rate of the crude oil, and the temperature and pressure in the absorption test in the absorption tester 1 (step S13). As described above, the absorption process in the absorption tester is simulated by the simulation function (absorption process simulation method) at step S13.

The composition of the treated gas analyzed is then compared with the composition of the treated gas calculated by simulation (step S14). It is then determined whether the composition of the treated gas analyzed agrees with the composition of the treated gas calculated by simulation (step S15). If it is determined that they agree ("Yes"), it is determined that the input composition of the crude oil is correct. The result obtained by the simulation function is then output to the display unit 43 (step S17). Specifically, the result obtained by the simulation function is output, for example, to the display unit 43 as the data listed in Table 3.

If it is determined that they do not agree ("No"), it is determined that the input composition of the crude oil deviates from the actual composition of the crude oil. As previously mentioned, crude oil is thought to have the absorption capacity equivalent to the amount of reduction in concentration for each component of the test gas. Based on this, if the composition of the treated gas analyzed does not agree with the composition of the treated gas calculated by simulation, it can be thought that the simulated absorption capacity of the crude oil deviates from the actual absorption capacity of the crude oil. That is, the input composition of the crude oil is thought to deviate from the actual composition of the crude oil.

If it is determined that they do not agree, the concentration of a component that deviates in the input composition of the crude oil is corrected (step S16). Specifically, the concentration for each component of the crude oil is reexamined and corrected based on the difference between the concentration for each component of the test gas and the concentration for each component of the treated gas. Returning to step S13, simulation is performed again. The process from step S13 to step S16 is thus repeated for calibration until the difference between the composition of the treated gas analyzed and the composition of the treated gas calculated by simulation converges. The composition of crude oil is thus estimated by the crude oil composition estimation method.

TABLE 3

| | | Stream name | | | |
|---|---|---|---|---|---|
| | | Absorption column inlet | Absorption column outlet | Crude oil inlet | Crude oil outlet |
| | Temperature (° C.) | 20.67783 | 16.43407 | 15 | 19.33984 |
| | Phase (vapor phase/liquid phase) | Vapor phase | Vapor phase | Liquid phase | Liquid phase |
| | Composition (mole fraction) | Analyzed value | Calculated value | Input value | Calculated value |
| Gas | Nitrogen | 0.588754 | 0.735991 | 0 | 0.003424 |
| | Oxygen | 0.119145 | 0.118952 | 0 | 0.008217 |
| | Carbon dioxide | 0.031224 | 0.038564 | 0 | 0.000299 |
| C1 | Methane | 0.015076 | 0.017561 | 0 | 0.00041 |
| C2 | Ethane | 0.021838 | 0.015004 | 0 | 0.003212 |
| C3 | Propane | 0.071393 | 0.025258 | 0.009009 | 0.024861 |
| C4 | i-Butane | 0.027045 | 0.011045 | 0.016016 | 0.020787 |
| | n-Butane | 0.065628 | 0.018651 | 0.041041 | 0.054513 |
| C5 | i-Pentane | 0.021495 | 0.006851 | 0.042042 | 0.044308 |
| | n-Pentane | 0.021648 | 0.007266 | 0.054054 | 0.055029 |
| | 2,2-Dimethylbutane | 0.000254 | 0.000000 | 0.006006 | 0.006087 |
| C6 | n-Hexane | 0.009258 | 0.001720 | 0.037037 | 0.037024 |
| | Cyclohexane | 0.005886 | 0.002170 | 0.045045 | 0.043293 |
| C7 | n-Heptane | 0.001093 | 0.000574 | 0.048048 | 0.044959 |
| | Methylcyclohexane | 0.000262 | 0.000173 | 0.015015 | 0.013983 |
| C8 | n-Octane | 0 | 2.60E−05 | 0.047047 | 0.043819 |
| | 1,2-Dimethylcyclohexane | 0 | 2.40E−05 | 0.018018 | 0.016782 |
| C9 | n-Nonane | 0 | 3.50E−05 | 0.03976 | 0.037032 |
| | 1,2,4-Trimethylcyclohexane | 0 | 5.44E−06 | 0.012012 | 0.011188 |
| C10 | n-Decane | 0 | 2.42E−06 | 0.008008 | 0.007459 |
| | 1,2,4-Diethylcyclohexane | 0 | 1.91E−07 | 0.001001 | 0.000932 |
| Hypothetical component represented by boiling point | Boiling point 51° C. | 0 | 0 | 0 | 0 |
| | Boiling point 77° C. | 0 | 0 | 0 | 0 |
| | Boiling point 101° C. | 0 | 0 | 0 | 0 |
| | Boiling point 128° C. | 0 | 0 | 0 | 0 |
| | Boiling point 155° C. | 0 | 0 | 0 | 0 |
| | Boiling point 184° C. | 0 | 1.88E−05 | 0.064064 | 0.059667 |
| | Boiling point 211° C. | 0 | 8.66E−06 | 0.097097 | 0.090438 |
| | Boiling point 238° C. | 0 | 9.12E−07 | 0.044044 | 0.041024 |
| | Boiling point 268° C. | 0 | 2.6E−07 | 0.022923 | 0.021351 |
| | Boiling point 295° C. | 0 | 3.64E−08 | 0.067467 | 0.062842 |
| | Boiling point 322° C. | 0 | 6.72E−09 | 0.064064 | 0.059672 |
| | Boiling point 351° C. | 0 | 1.75E−10 | 0.01001 | 0.009324 |
| | Boiling point 377° C. | 0 | 3.53E−11 | 0.025025 | 0.023309 |
| | Boiling point 408° C. | 0 | 1.46E−12 | 0.026026 | 0.024242 |
| | Boiling point 439° C. | 0 | 2.71E−13 | 0.041041 | 0.038227 |
| | Boiling point 494° C. | 0 | 2.05E−15 | 0.03003 | 0.027971 |
| | Boiling point 552° C. | 0 | 7.64E−19 | 0.01001 | 0.009324 |
| | Boiling point 602° C. | 0 | 1.36E−21 | 0.06006 | 0.055942 |
| | Boiling point 671° C. | 0 | 1.68E−25 | 0.002002 | 0.001865 |
| | Boiling point 781° C. | 0 | 0 | 0 | 0 |

Table 3 lists the result of simulating the material balance of an absorption process in an absorption test in which test gas at 20.7° C. was absorbed with crude oil at 15° C. Table 3 lists the analyzed composition of the test gas, the calculated composition of the treated gas, the input composition of crude oil, and the calculated composition of the gas-absorbed crude oil. In Table 3, the composition of the test gas is denoted as absorption column inlet, the composition of the treated gas is denoted as absorption column outlet, the composition of crude oil is denoted as crude oil inlet, and the composition of the gas-absorbed crude oil is denoted as crude oil outlet. The same applies to Table 4 and Table 5 described later.

In the absorption test under this condition, calibration was performed by correcting the concentration for each of $C_{3-10}$ components in the composition of the crude oil. Because the simulation is by vapor-liquid equilibrium calculation, a mole fraction value is calculated, though a slight amount, as the composition of the treated gas. However, the detection limit value of a gas chromatograph generally used is 0.1 mol %. That is, a component having a concentration smaller than 0.1 mol % is assumed to be zero in analysis by a gas chromatograph. In this absorption test, the concentration for each component with carbon number 8 or more is all calculated in mole fraction equal to or smaller than the detection limit value. The concentration for each component with carbon number 8 or more is therefore zero in analysis by a gas chromatograph. Hence, the concentration for each component with carbon number 8 or more of the treated gas all can be treated as zero. The concentration for each hypothetical component of the treated gas is all calculated in mole fraction, equal to or smaller than the detection limit value and therefore can be treated as zero as well. As described above, the result of the absorption test under this temperature condition is significantly manageable.

TABLE 4

| | | Stream name | | | |
|---|---|---|---|---|---|
| | | Absorption column inlet | Absorption column outlet | Crude oil inlet | Crude oil outlet |
| Temperature (° C.) | | 35.32648 | 31.71818 | 30 | 34.13586 |
| Phase (vapor phase/liquid phase) | | Vapor phase | Vapor phase | Liquid phase | Liquid phase |
| Composition (mole fraction) | | Analyzed value | Calculated value | Input value | Calculated value |
| Gas | Nitrogen | 0.538665 | 0.651724 | 0 | 0.003029 |
| | Oxygen | 0.145406 | 0.151497 | 0 | 0.008076 |
| | Carbon dioxide | 0.029975 | 0.035928 | 0 | 0.000269 |
| C1 | Methane | 0.015089 | 0.017338 | 0 | 0.000357 |
| C2 | Ethane | 0.024827 | 0.020420 | 0 | 0.002997 |
| C3 | Propane | 0.078105 | 0.041201 | 0.009009 | 0.024673 |
| C4 | i-Butane | 0.030446 | 0.017550 | 0.016016 | 0.020829 |
| | n-Butane | 0.070053 | 0.030574 | 0.041041 | 0.054745 |
| C5 | i-Pentane | 0.023868 | 0.011717 | 0.042042 | 0.044417 |
| | n-Pentane | 0.024555 | 0.012725 | 0.054054 | 0.055155 |
| | 2,2-Dimethylbutane | 0.000223 | 0.000001 | 0.006006 | 0.006087 |
| C6 | n-Hexane | 0.009596 | 0.003220 | 0.037037 | 0.037066 |
| | Cyclohexane | 0.006986 | 0.004006 | 0.045045 | 0.043343 |
| C7 | n-Heptane | 0.001553 | 0.001199 | 0.048048 | 0.044992 |
| | Methylcyclohexane | 0.000653 | 0.000651 | 0.015015 | 0.013993 |
| C8 | n-Octane | 0 | 8.60E−05 | 0.047047 | 0.043847 |
| | 1,2-Dimethylcyclohexane | 0 | 5.87E−05 | 0.018018 | 0.016793 |
| C9 | n-Nonane | 0 | 9.03E−05 | 0.03976 | 0.037056 |
| | 1,2,4-Trimethylcyclohexane | 0 | 1.42E−05 | 0.012012 | 0.011195 |
| C10 | n-Decane | 0 | 6.81E−06 | 0.008008 | 0.007464 |
| | 1,2,4-Diethylcyclohexane | 0 | 5.17E−07 | 0.001001 | 0.000933 |
| Hypothetical component represented by boiling point | Boiling point 51° C. | 0 | 0 | 0 | 0 |
| | Boiling point 77° C. | 0 | 0 | 0 | 0 |
| | Boiling point 101° C. | 0 | 0 | 0 | 0 |
| | Boiling point 128° C. | 0 | 0 | 0 | 0 |
| | Boiling point 155° C. | 0 | 0 | 0 | 0 |
| | Boiling point 184° C. | 0 | 5.15E−05 | 0.064064 | 0.059693 |
| | Boiling point 211° C. | 0 | 2.61E−05 | 0.097097 | 0.090488 |
| | Boiling point 238° C. | 0 | 3.08E−06 | 0.044044 | 0.041049 |
| | Boiling point 268° C. | 0 | 8.84E−07 | 0.022923 | 0.021364 |
| | Boiling point 295° C. | 0 | 1.64E−07 | 0.067467 | 0.06288 |
| | Boiling point 322° C. | 0 | 3.46E−08 | 0.064064 | 0.059708 |
| | Boiling point 351° C. | 0 | 1.04E−09 | 0.01001 | 0.009329 |
| | Boiling point 377° C. | 0 | 2.57E−10 | 0.025025 | 0.023324 |
| | Boiling point 408° C. | 0 | 1.38E−11 | 0.026026 | 0.024256 |
| | Boiling point 439° C. | 0 | 2.99E−12 | 0.041041 | 0.038251 |
| | Boiling point 494° C. | 0 | 3.31E−14 | 0.03003 | 0.027988 |
| | Boiling point 552° C. | 0 | 2.08E−17 | 0.01001 | 0.009329 |
| | Boiling point 602° C. | 0 | 7.07E−20 | 0.06006 | 0.055977 |
| | Boiling point 671° C. | 0 | 1.45E−23 | 0.002002 | 0.001866 |
| | Boiling point 781° C. | 0 | 0 | 0 | 0 |

Table 4 lists the result obtained by the absorption process simulation method by performing an absorption test on the same crude oil as in Table 3, in which test gas at 35.3° C. was absorbed with crude oil at 30° C. Table 4 lists the composition of the test gas, the composition of the treated gas, the composition of the crude oil, and the composition of the gas-absorbed crude oil.

In the absorption test under this condition, the calculated values of the composition of the treated gas are consistent with the analyzed values. The concentration for each component with carbon number 8 or more all can be treated as zero in the same manner as in Table 3. The concentration for each hypothetical component of the treated gas is all calculated in mole fraction equal to or smaller than the detection limit value and therefore all can be treated as zero as well.

In the absorption process simulation method in an absorption and liquefaction system, the absorption process in an absorption and liquefaction system is simulated under changed conditions including the size of the absorption and liquefaction system, the flow rate of vapors, the flow rate of crude oil, temperature, and pressure, based on the composition of crude oil estimated by the crude oil composition estimation method and the composition of vapors. By comparing the simulation results under changed conditions, the size of the absorption and liquefaction system, the flow rate of vapors, the flow rate of crude oil, temperature, and pressure can be appropriately set.

In the process simulation method in a recovery system, the overall process in a recovery system is simulated, which recovers vapors by a membrane separation process of allowing hydrocarbons to selectively pass through or a gas separation process using an adsorbent selectively adsorbing hydrocarbons, in combination with the absorption process simulated by the absorption process simulation method in an absorption and liquefaction system. The overall process of the vapor recovery system is thus simulated.

In the crude oil composition estimation method as described above, the concentration for each composition of crude oil can be estimated precisely based on the difference between the concentration for each component of test gas and the concentration for each component of treated gas in an absorption test. That is, the concentration for each component of crude oil in the liquid phase can be estimated precisely by the crude oil composition estimating function based on data in the vapor phase in an absorption test.

In the absorption process simulation method in an absorption and liquefaction system, an absorption process is simulated based on the precise concentration for each component of crude oil that is estimated by the crude oil composition estimation method, thereby improving the precision of simulation. The size of the absorption and liquefaction system, the flow rate of vapors, the flow rate of crude oil, temperature, and pressure thus can be set appropriately. Accordingly, the recovery ratio of crude oil in the absorption and liquefaction system can be increased, and the concentration of emitted vapors can be reduced.

Figure 7:
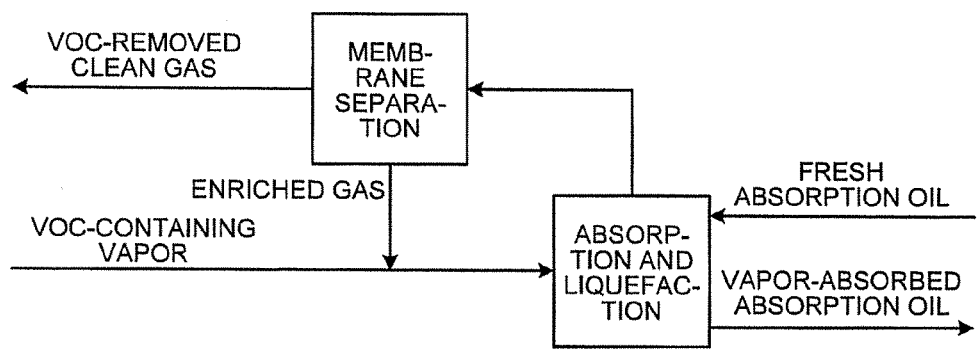
FIG. 7 is a block diagram illustrating an overview of an absorption process in a conventional absorption and liquefaction system.

In the process simulation method in a recovery system, the overall process in a recovery system can be simulated, which recovers vapors by a membrane separation process or a gas separation process using an adsorbent, in combination with the absorption process simulated by the absorption process simulation method in an absorption and liquefaction system based on the concentration for each component of crude oil estimated by the crude oil composition estimation method. The membrane separation process requires repeated calculations in a simulation because enriched gas merges into vapors as illustrated in FIG. 7. The repeated calculations can converge in a single simulation. As described above, the entire vapor recovery system can be designed appropriately.

Table 5 lists, as a comparative example, the simulation result obtained by creating hypothetical components with the crude oil simulated composition creating function of the process simulator 40 based on distillation curve, API gravity, and RVP vapor pressure, and using the created hypothetical components as the input values to the simulation function of the process simulator 40. That is, the composition of crude oil is not estimated by the crude oil composition estimation method. Open data that provides the concentrations for $C_{3-5}$ components were also referred to. Table 5 lists the composition of test gas, the composition of treated gas, the composition of crude oil, and the composition of gas-absorbed crude oil.

TABLE 5

| | | Stream name | | | |
|---|---|---|---|---|---|
| | | Absorption column inlet | Absorption column outlet | Crude oil inlet | Crude oil outlet |
| Temperature (° C.) | | 9 | 3.194336 | 3 | 4.545685 |
| Phase (vapor phase/liquid phase) | | Vapor phase | Vapor phase | Liquid phase | Liquid phase |
| Composition (mole fraction) | | Analyzed value | Calculated value | Input value | Calculated value |
| Gas | Nitrogen | 0.727307 | 0.799354 | 0 | 0.004095 |
| | Oxygen | 0.044983 | 0.048978 | 0 | 0.000428 |
| | Carbon dioxide | 0.111194 | 0.114051 | 0 | 0.009329 |
| C1 | Methane | 0.000708 | 0.000749 | 0 | 2.12E−05 |
| C2 | Ethane | 0.002224 | 0.001983 | 0 | 0.000461 |
| C3 | Propane | 0.018397 | 0.009195 | 0.005100 | 0.010043 |
| C4 | i-Butane | 0.019408 | 0.012431 | 0.044534 | 0.045854 |
| | n-Butane | 0.019408 | 0.004306 | 0.006437 | 0.013561 |
| C5 | i-Pentane | 0.016477 | 0.002413 | 0.031764 | 0.036737 |
| | n-Pentane | 0.016477 | 0.001785 | 0.015291 | 0.021431 |
| C6 | n-Hexane | 0.014152 | 0.000077 | 0 | 0.006568 |
| C7 | n-Heptane | 0.00091 | 0.000001 | 0 | 0.000423 |
| Hypothetical component represented by boiling point | Boiling point 51° C. | 0 | 0.000752 | 0.019771 | 0.018397 |
| | Boiling point 77° C. | 0 | 0.001112 | 0.059830 | 0.056195 |
| | Boiling point 101° C. | 0 | 0.000376 | 0.060019 | 0.056708 |
| | Boiling point 128° C. | 0 | 0.000187 | 0.095079 | 0.090021 |
| | Boiling point 155° C. | 0 | 5.20E−05 | 0.091457 | 0.086652 |
| | Boiling point 184° C. | 0 | 9.21E−06 | 0.067930 | 0.064375 |
| | Boiling point 211° C. | 0 | 1.92E−06 | 0.066405 | 0.062933 |
| | Boiling point 238° C. | 0 | 3.80E−07 | 0.064585 | 0.061209 |
| | Boiling point 268° C. | 0 | 4.94E−08 | 0.047374 | 0.044898 |
| | Boiling point 295° C. | 0 | 5.83E−09 | 0.038176 | 0.036181 |
| | Boiling point 322° C. | 0 | 7.23E−10 | 0.037637 | 0.035670 |
| | Boiling point 351° C. | 0 | 8.60E−11 | 0.040019 | 0.037927 |
| | Boiling point 377° C. | 0 | 7.03E−12 | 0.034076 | 0.032295 |
| | Boiling point 408° C. | 0 | 4.12E−13 | 0.026718 | 0.025322 |
| | Boiling point 439° C. | 0 | 2.07E−14 | 0.032825 | 0.031110 |
| | Boiling point 494° C. | 0 | 1.34E−16 | 0.036295 | 0.034398 |
| | Boiling point 552° C. | 0 | 9.40E−20 | 0.027908 | 0.026450 |
| | Boiling point 602° C. | 0 | 2.27E−23 | 0.018137 | 0.017189 |
| | Boiling point 671° C. | 0 | 2.41E−27 | 0.014983 | 0.014200 |
| | Boiling point 781° C. | 0 | 1.37E−32 | 0.014173 | 0.013432 |

In this comparative example, the concentrations of $C_6$ n-hexane and $C_7$ n-heptane in crude oil are calculated to be zero, that is, not present in crude oil. It is thus demonstrated that a large part of n-hexane and n-heptane in the test gas is absorbed in the gas-absorbed crude oil. The hypothetical components of boiling point 51° C. to boiling point 128° C. are thought to correspond to around $C_{6-8}$ hydrocarbon components. It is demonstrated that these hypothetical components evaporate in the vapor phase from crude oil because they are not present in the test gas.

As described above, in the comparative example, the simulation result does not represent the actual state. The comparison with the analyzed value is therefore difficult.

The hypothetical components were substituted with hydrocarbon components after the simulation but did not match. The $C_{3-5}$ composition included in the open data differs from the composition calibrated by the crude oil composition estimation method of the present invention, and if it is used as it is, the precision of simulation is deteriorated.

As described above, simulation without estimating the composition of crude oil by the crude oil composition estimation method has poor precision.

The crude oil composition estimation method, the absorption process simulation method in an absorption and liquefaction system, and the process simulation method in a recovery system according to an embodiment of the present invention as described above are not limited to the foregoing embodiment and is susceptible to various modifications within the scope described in the claims.

In the present embodiment, the concentrations of $C_{1-10}$ hypothetical components are substituted with the concentrations of hydrocarbon components. However, the concentrations of all of the hypothetical components may be substituted with the concentrations of hydrocarbon components. Alternatively, the concentrations of $C_{1-8}$ hypothetical components may be substituted with the concentrations of the corresponding hydrocarbon components. In this case, the concentrations of $C_{9-10}$ hypothetical components are kept to the values created by the crude oil simulated composition creating function of the process simulator 40. This is because the $C_{9-10}$ hypothetical components do not affect the simulation. The concentrations of the $C_{9-10}$ hypothetical components act as a buffer zone when the concentration for each component is calculated in a simulation.

When the concentrations of hypothetical components are substituted with the concentrations of hydrocarbon components, a crude oil composition table open to public is referred to, thereby improving the precision of the composition of crude oil serving as an input value to the simulation function of the process simulator 40.

In the foregoing description, respective pairs of the concentration for each component of test gas and the concentration for each component of treated gas are acquired at a plurality of temperatures by changing temperature conditions. However, the pressure conditions may be changed. In this case, in the crude oil composition estimation method, the pressures are changed when vapors are absorbed with crude oil, and respective pairs of the concentration for each component of test gas and the concentration for each component of treated gas are acquired under a plurality of pressures. The concentrations of some components included in crude oil are estimated based on the difference between the concentration for each component of test gas and the concentration for each component of treated gas under a first pressure, and the concentrations of other components included crude oil are estimated based on the difference between the concentration for each component of test gas and the concentration for each component of treated gas under a pressure different from the first pressure. Specifically, the pressure in the absorption operation is set such that the absorption efficiency is reduced when compared with that in the absorption test under a pressure condition of the first pressure. By doing so, the concentrations of the corresponding components of the treated gas are greater than zero.

Figure 4:
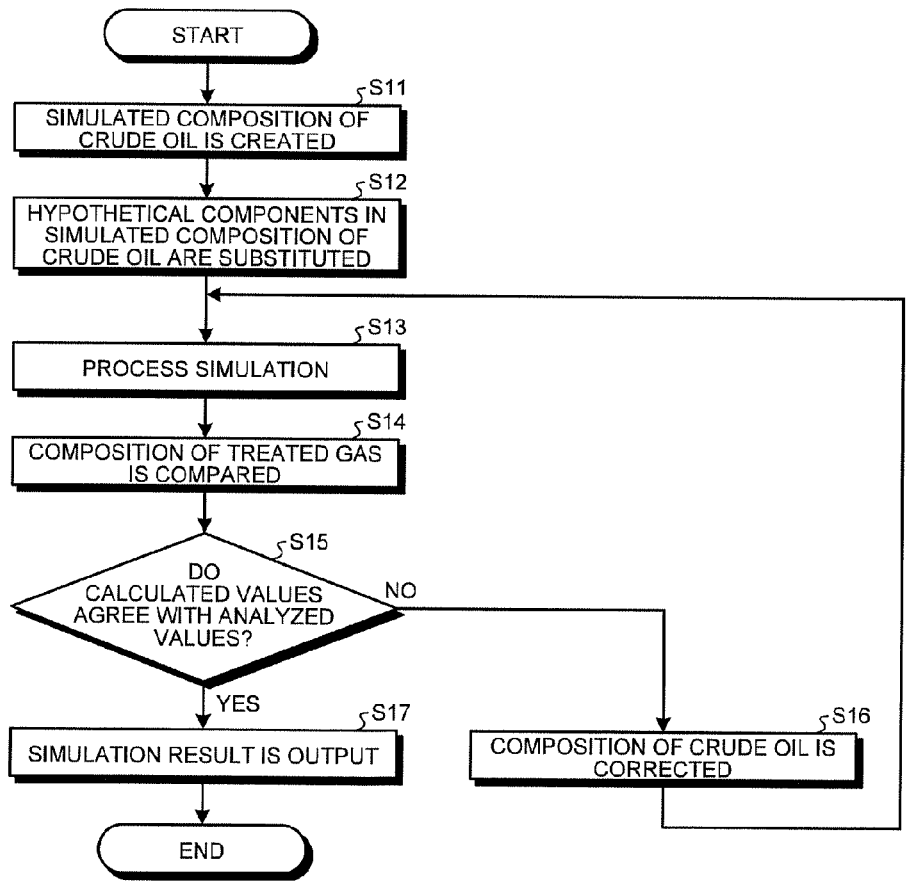
FIG. 4 is a flowchart illustrating information processing in the process simulator.
Figure 5:
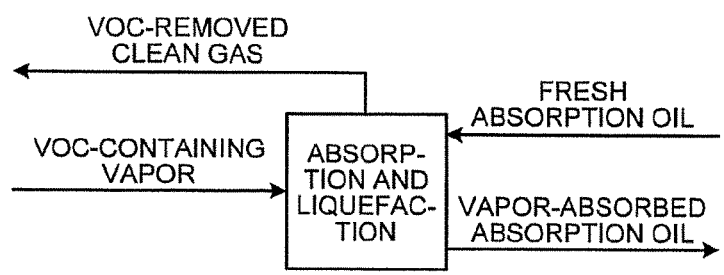
FIG. 5 is a block diagram illustrating an overview of an absorption process in a conventional absorption and liquefaction system.
Figure 6:
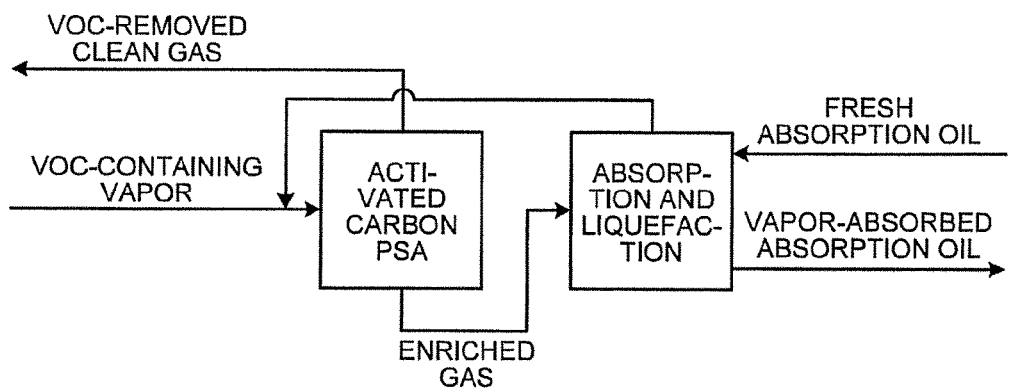
FIG. 6 is a block diagram illustrating an overview of an absorption process in a conventional absorption and liquefaction system.

In the absence of the crude oil composition estimating function, the composition of crude oil may be estimated by correcting the composition of crude oil serving as an input value to the simulation function, by trial and error. Specifically, the amount of absorption per hour for each component is calculated based on the concentration for each component of treated gas, the flow rate of treated gas, the concentration for each component of test gas, and the flow rate of test gas. The relation between the liquid-phase concentrations and the vapor-phase concentration for each component is calculated based on the solubility (absorption capacity) for each component in the liquid phase as a whole. The sum of amounts originally present in the vapor phase or the liquid phase is redistributed for each component according to the relation, whereby the composition of crude oil is estimated. The estimated composition of crude oil is then used as an input value to the simulation function. The process from step S13 to step S16 in the procedure illustrated in FIG. 4 is repeated for calibration until the difference between the composition of treated gas analyzed and the composition of treated gas calculated by simulation converges. The composition of crude oil may be estimated in this manner.

In the crude oil composition estimation method, the concentration for each component included in crude oil is estimated based on the difference between the concentration for each component of test gas of vapors and the concentration for each component of treated gas discharged after part of the test gas is absorbed with the crude oil. This achieves the effect of estimating the composition of crude oil from the concentration for each component in the vapor phase.

In the absorption process simulation method in an absorption and liquefaction system, the material balance of an absorption process in an absorption and liquefaction system is simulated based on the composition of crude oil estimated by the crude oil composition estimation method and the concentration for each component of vapors absorbed and liquefied in the absorption and liquefaction system. This achieves the effect of obtaining a precise simulation result.

In the process simulation method in a recovery system, an overall process in a recovery system can be simulated, which recovers vapors by a membrane separation process of allowing hydrocarbons to selectively pass through or a gas separation process using an adsorbent selectively adsorbing hydrocarbons, in combination with the absorption process of absorbing vapors with crude oil to be simulated by the absorption process simulation method in an absorption and liquefaction system. This achieves the effect of obtaining a precise simulation result.

In the method of producing an absorption and liquefaction system, the material balance of an absorption process in an absorption and liquefaction system is simulated, under changed conditions including a size of the absorption and liquefaction system, a flow rate of vapors, a flow rate of crude oil, temperature, and pressure, by the absorption process simulation method in an absorption and liquefaction system, thereby obtaining a precise simulation result. This achieves the effect of producing an absorption and liquefaction system with specifications determined appropriately.

In the method of producing a recovery system, an overall process in a recovery system is simulated by the process simulation method in a recovery system, thereby obtaining a precise simulation result. This achieves the effect of producing a recovery system with specifications determined appropriately.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A crude oil composition estimation method of estimating a composition of crude oil for use in simulation of a material balance in an absorption and liquefaction system that absorbs vapors emitted from the crude oil with the crude oil, the crude oil composition estimation method comprising:

performing an absorption test of absorbing test gas of the vapors with the crude oil and measuring concentration for each component of the test gas and concentration for each component of treated gas discharged after part of the test gas is absorbed with the crude oil;

creating a simulated composition of the crude oil with a composition of a concentration for each hypothetical component represented by a boiling point, based on crude oil open data indicating properties of the crude oil;

setting a concentration for each component included in the crude oil obtained by substituting hypothetical components of the created simulated composition of the crude oil with respective corresponding actual hydrocarbon components, as input values to a simulation;

simulating a material balance of an absorption process of absorbing the test gas with the crude oil in the absorption test, based on the concentration for each component included in the crude oil and the concentration for each component of the test gas measured in the absorption test;

comparing the concentration for each component of the treated gas calculated by the simulation with the concentration for each component of the treated gas measured in the absorption test;

estimating, at a time the concentration for each component of the treated gas calculated by the simulation agrees with the concentration for each component of the treated gas measured in the absorption test, that the concentration for each component included in the crude oil is a correct crude oil composition; and repeating, at a time the concentration for each component of the treated gas calculated by the simulation does not agree with the concentration for each component of the treated gas measured in the absorption test, a process of correcting the concentration for each component included in the crude oil and then comparing the concentration for each component of the treated gas calculated by the simulation with the concentration for each component of the treated gas measured in the absorption test, until the concentration for each component of the treated gas calculated by the simulation agrees with the concentration for each component of the treated gas measured in the absorption test, and, at a time there is an agreement, estimating that the corrected concentration for each component included in the crude oil is a correct crude oil composition.

2. The crude oil composition estimation method according to claim 1, wherein at the creating of a simulated composition of the crude oil with a composition of concentration for each hypothetical component represented by a boiling point based on crude oil open data, and the setting of a concentration for each component included in the crude oil obtained by substituting hypothetical components of the created simulated composition of the crude oil with respective corresponding actual hydrocarbon components, as input values to a simulation, $C_{1-10}$ hypothetical components, of the hypothetical components of the crude oil, are substituted with respective corresponding actual hydrocarbon components.

3. An absorption process simulation method in an absorption and liquefaction system, the absorption process simulation method comprising:

simulating a material balance of a process in the absorption and liquefaction system under changed conditions including a size of the absorption and liquefaction system, a flow rate of vapors absorbed and liquefied in the absorption and liquefaction system, a flow rate of crude oil, temperature, and pressure, based on a concentration for each component of the vapors and a composition of the crude oil estimated by a crude oil composition estimation method, the crude oil composition estimation method including:

performing an absorption test of absorbing test gas of the vapors with the crude oil and measuring concentration for each component of the test gas and concentration for each component of treated gas discharged after part of the test gas is absorbed with the crude oil;

creating a simulated composition of the crude oil with a composition of a concentration for each hypothetical component represented by a boiling point, based on crude oil open data indicating properties of the crude oil;

setting a concentration for each component included in the crude oil obtained by substituting hypothetical components of the created simulated composition of the crude oil with respective corresponding actual hydrocarbon components, as input values to a simulation;

simulating a material balance of an absorption process of absorbing the test gas with the crude oil in the absorption test, based on the concentration for each component included in the crude oil and the concentration for each component of the test gas measured in the absorption test;

comparing the concentration for each component of the treated gas calculated by the simulation with the concentration for each component of the treated gas measured in the absorption test;

estimating, at a time the concentration for each component of the treated gas calculated by the simulation agrees with the concentration for each component of the treated gas measured in the absorption test, that the concentration for each component included in the crude oil is a correct crude oil composition; and repeating, at a time the concentration for each component of the treated gas calculated by the simulation does not agree with the concentration for each component of the treated gas measured in the absorption test, a process of correcting the concentration for each component included in the crude oil and then comparing the concentration for each component of the treated gas calculated by the simulation with the concentration for each component of the treated gas measured in the absorption test, until the concentration for each component of the treated gas calculated by the simulation agrees with the concentration for each component of the treated gas measured in the absorption test, and, at a time there is an agreement, estimating that the corrected concentration for each component included in the crude oil is a correct crude oil composition.

4. The absorption process simulation method according to claim 3, wherein at the creating of a simulated composition of the crude oil with a composition of concentration for each hypothetical component represented by a boiling point based on crude oil open data, and the setting of a concentration for each component included in the crude oil obtained by substituting hypothetical components of the created simulated composition of the crude oil with respective corresponding actual hydrocarbon components, as input values to a simulation, $C_{1-10}$ hypothetical components, of the hypothetical components of the crude oil, are substituted with respective corresponding actual hydrocarbon components.

5. A process simulation method in a recovery system, the process simulation method comprising:
simulating an overall process in the recovery system that recovers vapors by a membrane separation process of allowing hydrocarbons to selectively pass through or a gas separation process using an adsorbent selectively adsorbing hydrocarbons, in combination with an absorption process of absorbing the vapors with the crude oil that is simulated by an absorption process simulation method in an absorption and liquefaction system, the absorption process simulation method including:
simulating a material balance of a process in the absorption and liquefaction system under changed conditions including a size of the absorption and liquefaction system, a flow rate of vapors absorbed and liquefied in the absorption and liquefaction system, a flow rate of crude oil, temperature, and pressure, based on a concentration for each component of the vapors and a composition of the crude oil estimated by a crude oil composition estimation method, the crude oil composition estimation method including:
performing an absorption test of absorbing test gas of the vapors with the crude oil and measuring concentration for each component of the test gas and concentration for each component of treated gas discharged after part of the test gas is absorbed with the crude oil;
creating a simulated composition of the crude oil with a composition of a concentration for each hypothetical component represented by a boiling point, based on crude oil open data indicating properties of the crude oil;
setting a concentration for each component included in the crude oil obtained by substituting hypothetical components of the created simulated composition of the crude oil with respective corresponding actual hydrocarbon components, as input values to a simulation;
simulating a material balance of an absorption process of absorbing the test gas with the crude oil in the absorption test, based on the concentration for each component included in the crude oil and the concentration for each component of the test gas measured in the absorption test;
comparing the concentration for each component of the treated gas calculated by the simulation with the concentration for each component of the treated gas measured in the absorption test;
estimating, at a time the concentration for each component of the treated gas calculated by the simulation agrees with the concentration for each component of the treated gas measured in the absorption test, that the concentration for each component included in the crude oil is a correct crude oil composition; and
repeating, at a time the concentration for each component of the treated gas calculated by the simulation does not agree with the concentration for each component of the treated gas measured in the absorption test, a process of correcting the concentration for each component included in the crude oil and then comparing the concentration for each component of the treated gas calculated by the simulation with the concentration for each component of the treated gas measured in the absorption test, until the concentration for each component of the treated gas calculated by the simulation agrees with the concentration for each component of the treated gas measured in the absorption test, and, at a time there is an agreement, estimating that the corrected concentration for each component included in the crude oil is a correct crude oil composition.

6. The process simulation method according to claim 5, wherein at the creating of a simulated composition of the crude oil with a composition of concentration for each hypothetical component represented by a boiling point based on crude oil open data, and the setting of a concentration for each component included in the crude oil obtained by substituting hypothetical components of the created simulated composition of the crude oil with respective corresponding actual hydrocarbon components, as input values to a simulation, $C_{1-10}$ hypothetical components, of the hypothetical components of the crude oil, are substituted with respective corresponding actual hydrocarbon components.

7. A method of producing an absorption and liquefaction system, the method comprising:
simulating a material balance of an absorption process in the absorption and liquefaction system under changed conditions including a size of the absorption and liquefaction system, a flow rate of the vapors, a flow rate of the crude oil, temperature, and pressure, by an absorption process simulation method in the absorption and liquefaction system; and
producing the absorption and liquefaction system with specifications determined based on a result of the simulation,
wherein the absorption process simulation method includes:
simulating a material balance of a process in the absorption and liquefaction system under changed conditions including a size of the absorption and liquefaction system, a flow rate of vapors absorbed and liquefied in the absorption and liquefaction system, a flow rate of crude oil, temperature, and pressure, based on a concentration for each component of the vapors and a composition of the crude oil estimated by a crude oil composition estimation method, the crude oil composition estimation method including:
performing an absorption test of absorbing test gas of the vapors with the crude oil and measuring concentration for each component of the test gas and concentration for each component of treated gas discharged after part of the test gas is absorbed with the crude oil;
creating a simulated composition of the crude oil with a composition of a concentration for each hypothetical component represented by a boiling point, based on crude oil open data indicating properties of the crude oil;
setting a concentration for each component included in the crude oil obtained by substituting hypothetical components of the created simulated composition of the crude oil with respective corresponding actual hydrocarbon components, as input values to a simulation;

simulating a material balance of an absorption process of absorbing the test gas with the crude oil in the absorption test, based on the concentration for each component included in the crude oil and the concentration for each component of the test gas measured in the absorption test;

comparing the concentration for each component of the treated gas calculated by the simulation with the concentration for each component of the treated gas measured in the absorption test;

estimating, at a time the concentration for each component of the treated gas calculated by the simulation agrees with the concentration for each component of the treated gas measured in the absorption test, that the concentration for each component included in the crude oil is a correct crude oil composition; and repeating, at a time the concentration for each component of the treated gas calculated by the simulation does not agree with the concentration for each component of the treated gas measured in the absorption test, a process of correcting the concentration for each component included in the crude oil and then comparing the concentration for each component of the treated gas calculated by the simulation with the concentration for each component of the treated gas measured in the absorption test, until the concentration for each component of the treated gas calculated by the simulation agrees with the concentration for each component of the treated gas measured in the absorption test, and, at a time there is an agreement, estimating that the corrected concentration for each component included in the crude oil is a correct crude oil composition.

8. The method of producing an absorption and liquefaction system according to claim 7, wherein at the creating of a simulated composition of the crude oil with a composition of concentration for each hypothetical component represented by a boiling point based on crude oil open data, and the setting of a concentration for each component included in the crude oil obtained by substituting hypothetical components of the created simulated composition of the crude oil with respective corresponding actual hydrocarbon components, as input values to a simulation, $C_{1-10}$ hypothetical components, of the hypothetical components of the crude oil, are substituted with respective corresponding actual hydrocarbon components.

9. A method of producing a recovery system, the method comprising:
    simulating an overall process in the recovery system by a process simulation method in a recovery system; and
    producing the recovery system with specifications determined based on a result of the simulation,
    wherein the process simulation method includes:
        simulating an overall process in the recovery system that recovers vapors by a membrane separation process of allowing hydrocarbons to selectively pass through or a gas separation process using an adsorbent selectively adsorbing hydrocarbons, in combination with an absorption process of absorbing the vapors with the crude oil that is simulated by an absorption process simulation method in an absorption and liquefaction system, the absorption process simulation method including:
            simulating a material balance of a process in the absorption and liquefaction system under changed conditions including a size of the absorption and liquefaction system, a flow rate of vapors absorbed and liquefied in the absorption and liquefaction system, a flow rate of crude oil, temperature, and pressure, based on a concentration for each component of the vapors and a composition of the crude oil estimated by a crude oil composition estimation method, the crude oil composition estimation method including:
                performing an absorption test of absorbing test gas of the vapors with the crude oil and measuring concentration for each component of the test gas and concentration for each component of treated gas discharged after part of the test gas is absorbed with the crude oil;
                creating a simulated composition of the crude oil with a composition of a concentration for each hypothetical component represented by a boiling point, based on crude oil open data indicating properties of the crude oil;
                setting a concentration for each component included in the crude oil obtained by substituting hypothetical components of the created simulated composition of the crude oil with respective corresponding actual hydrocarbon components, as input values to a simulation;
                simulating a material balance of an absorption process of absorbing the test gas with the crude oil in the absorption test, based on the concentration for each component included in the crude oil and the concentration for each component of the test gas measured in the absorption test;
                comparing the concentration for each component of the treated gas calculated by the simulation with the concentration for each component of the treated gas measured in the absorption test;
                estimating, at a time the concentration for each component of the treated gas calculated by the simulation agrees with the concentration for each component of the treated gas measured in the absorption test, that the concentration for each component included in the crude oil is a correct crude oil composition; and
                repeating, at a time the concentration for each component of the treated gas calculated by the simulation does not agree with the concentration for each component of the treated gas measured in the absorption test, a process of correcting the concentration for each component included in the crude oil and then comparing the concentration for each component of the treated gas calculated by the simulation with the concentration for each component of the treated gas measured in the absorption test, until the concentration for each component of the treated gas calculated by the simulation agrees with the concentration for each component of the treated gas measured in the absorption test, and, at a time there is an agreement, estimating that the corrected concentration for each component included in the crude oil is a correct crude oil composition.

10. The method of producing a recovery system according to claim 9, wherein at the creating of a simulated composition of the crude oil with a composition of concentration for each hypothetical component represented by a boiling point based on crude oil open data, and the setting of a concentration for each component included in the crude oil obtained by substituting hypothetical components of the created simulated composition of the crude oil with respective corresponding actual hydrocarbon components, as input values to a simulation, $C_{1-10}$ hypothetical components, of the hypothetical components of the crude oil, are substituted with respective corresponding actual hydrocarbon components.

\* \* \* \* \*